United States Patent [19]

Bains

[11] Patent Number: 4,550,605
[45] Date of Patent: Nov. 5, 1985

[54] HOPPING MECHANISM FOR PIPE AND COUPLING INSPECTION PROBE

[75] Inventor: Elizabeth M. Bains, Pearland, Tex.

[73] Assignee: AMF Inc., White Plains, N.Y.

[21] Appl. No.: 641,090

[22] Filed: Aug. 15, 1984

[51] Int. Cl.$^4$ .................. G01N 29/04; G01N 27/82
[52] U.S. Cl. ........................................ 73/622; 73/637; 73/638; 324/220; 324/221; 324/243
[58] Field of Search ............... 324/219, 220, 221, 243; 73/622, 623, 637, 638

[56] References Cited

U.S. PATENT DOCUMENTS

| | | | |
|---|---|---|---|
| 3,066,254 | 11/1962 | Price et al. | 324/243 |
| 4,213,345 | 7/1980 | Dufour | 73/638 |
| 4,474,064 | 10/1984 | Narusa et al. | 73/622 |

*Primary Examiner*—Howard A. Birmiel
*Attorney, Agent, or Firm*—David E. Dougherty; John H. Gallagher

[57] ABSTRACT

The invention relates to nondestructive inspection apparatus for automatically inspecting the end region of a tubular member and a coupling member secured to that end region. An inspection probe is yieldingly received within a housing that is pivotally supported on an arm that moves helically around the tubular member. The probe is extended outwardly from an air chamber in the housing to contact the surface of the tubular member. When the probe encounters the obstructing shoulder of the coupling on the end of the tubular member, the housing is caused to pivot to activate an air escape mechanism to reduce the air pressure in the chamber and cause the probe to be withdrawn radially to hop over the obstructing shoulder on the coupling. The housing then returns to its original position to terminate the air escape from the chamber. Air pressure builds up again to force the probe outwardly onto the surface of the coupling.

11 Claims, 5 Drawing Figures

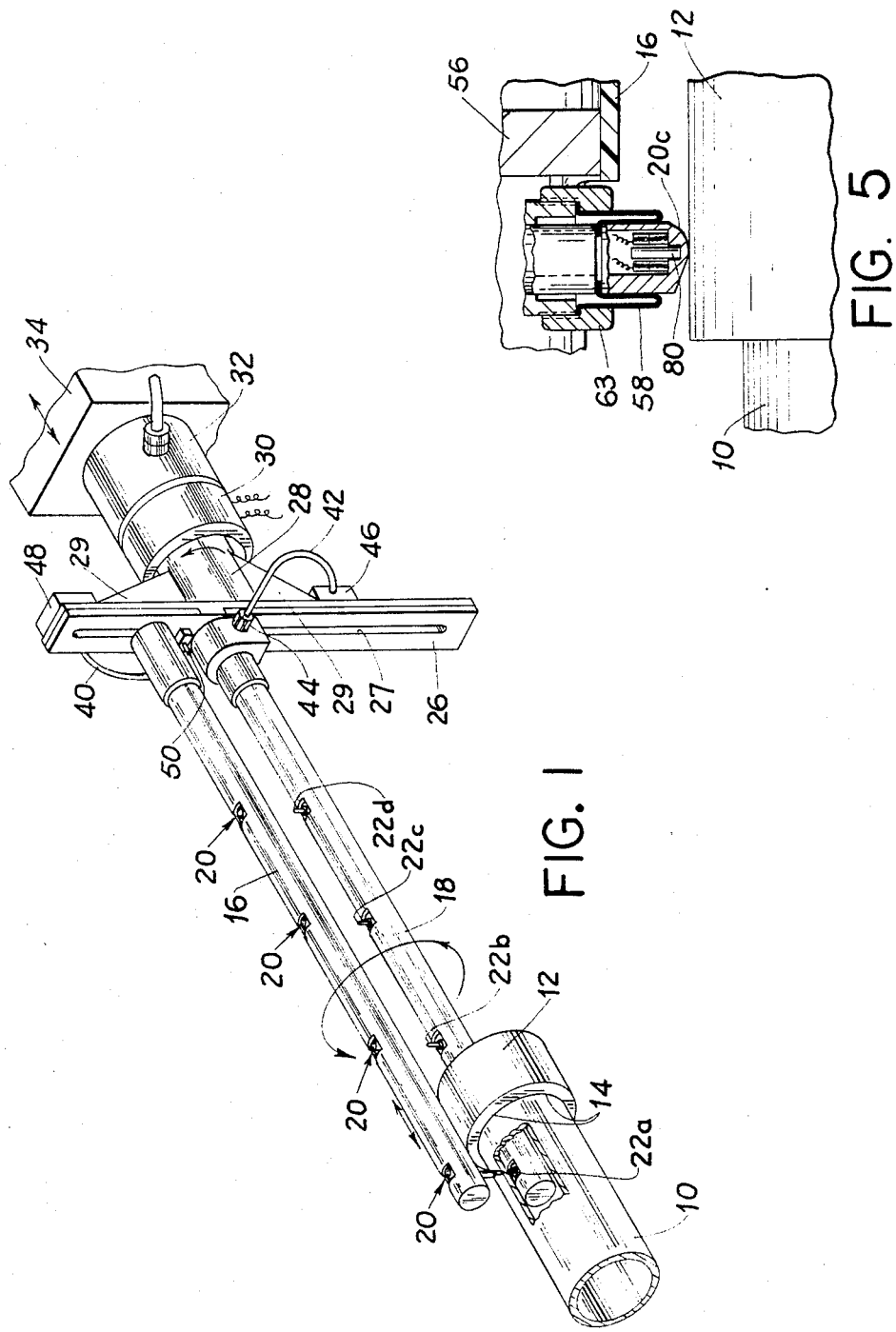

HOPPING MECHANISM FOR PIPE AND COUPLING INSPECTION PROBE

BACKGROUND OF THE INVENTION

The American Petroleum Institute (API) has set industry standards for the nondestructive inspection of oil field tubular goods. The standard as to whether a flaw in the wall of a pipe is acceptable or unacceptable is based on the depth of the flaw as a percentage of the wall thickness of the pipe. For threaded couplings that join pipes together, the standard for acceptability or unacceptability is based on the absolute depth of the flaw, irrespective of the wall thickness of the coupling. Oil field casing and tubing supplied by a pipe manufacturer commonly is threaded at both ends and one of the ends has an internally threaded coupling member secured to, or made up on, one end of the casing or tubing. Similarly, used casing and tubing available in the field commonly has a coupling threaded onto one end of the tubular member. API inspection standards require that any flaw that extends from the body of the tubular member under the end of the threaded coupling be considered a reject, regardless of the depth or nature of the flaw. This requirement stems from the fact that such a flaw may extend into the threaded region of the member, which is considered to be a critical area in terms of joint strength and makeup integrity. Any flaw at the end of the coupling that extends axially at the end of the coupling also is considered unacceptable.

In the past, automatic or semi-automatic nondestructive inspection of tubular members having a coupling threaded thereon has been somewhat incomplete because the apparatus could not inspect the region of the pipe immediately adjacent the inward end of the threaded coupling, and could not inspect the adjacent end region of the coupling. Consequently, the inspection results produced by automatic inspection equipment cannot be certified as meeting API standards, and the region immediately adjacent the end of the threaded coupling had to be inspected by an operator using a hand held inspection device. This manual inspection is quite time consuming, cumbersome, and can be dangerous to the operator when performed in a semi-automated inspection operation that involves a high volume of tubular members.

The present invention is a novel mechanism for permitting an eddy current probe of an automatic inspection apparatus to move very closely into the region between a pipe wall and the end of the coupling threaded thereon, and then to automatically hop over the end of the collar and come down at the very end of the top surface of the coupling. The invention thus enables an automatic end-area inspection apparatus to detect flaws at the inward end area of the coupling and in the pipe wall immediately adjacent thereto. This enables the detection of flaws that require an absolute rejection of that joint. Similarly, by being able to move in very close to the end of the coupling, the apparatus is able to determine that an acceptable flaw terminates just short of the end of the coupling and that the pipe is acceptable, rather than having to reject the pipe as it would if the inspection apparatus could not determine with certainty whether or not the flaw extended under the coupling.

BRIEF DESCRIPTION OF THE DRAWINGS

FIG. 1 is a simplified perspective view illustrating end area inspection apparatus that employs the mechanism of the present invention for permitting an inspection probe to move in extremely close to the end of a pipe coupling and automatically jump over that end and reposition itself on the top surface at the very end of the coupling;

FIGS. 3, 4, and 5 are simplified illustrations showing the inspection probe of this invention in various positions as it encounters and then hops over the end of the a coupling.

DESCRIPTION OF PREFERRED EMBODIMENT

Figure 3:
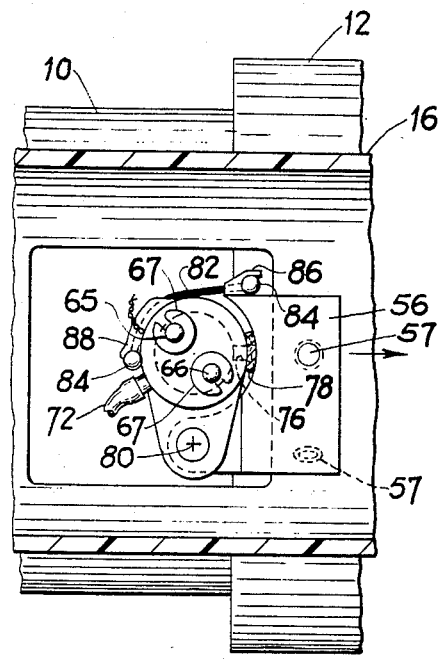

FIG. 1 is a simplified illustration of end area inspection apparatus in which the present invention is embodied. Tubular member 10 is externally threaded on its right end and a coupling 12 having internal threads is threaded onto the tubular member in a proper makeup according to API specifications. Tubular member 10 may be 30 feet long, for example, but the apparatus of FIG. 1 is intended to nondestructively inspect only the end region of the member and the coupling 12 secured thereto. The left end of tubular member 10, not illustrated, also is threaded but ordinarily will not have a coupling secured thereto. The inspection apparatus is comprised of two tubular arms 16 and 18 that may be made of a non-metallic material such as fiberglass. Arms 16 and 18 are adjustably positioned on transversely extending bracket member 26 that has a slot 27 therein. The right ends of arms 16 and 18 include releasable bracket members, not illustrated, that pass through slot 27 and hold the arms in fixed position relative to the bracket member 26. Arms 16 and 18 are spaced from each other so that arm 16 may be positioned closely adjacent the outer walls of a tubular member 10 and coupling 12 and arm 18 is positioned so that it is closely adjacent the inner walls of tubular member 10 and coupling 12. The positions of arms 16 and 18 on bracket 26 may be changed so that they can accomodate different size tubular goods.

Transversely extending bracket 26 is secured to a rotor member 28 by means of brackets 29. Rotor member 28 is coupled to the rotary drive shaft of an electrical motor 30 which rotates the rotor member 28, transverse bracket 26 and the arms 16 and 18 secured thereon. A slip ring-brush assembly 32 also is coupled to motor 30 and provides means for coupling inspection signals from the rotating apparatus. A support member 34 supports slip ring-brush assembly 32 and motor 30 and is adapted for forward and reverse translation in a direction parallel to the axis of tubular member 10. Support member 34 may be mounted on a rack and pinion mechanism, for example, that is actuated by a reversable DC motor.

In the preferred embodiment of the invention that will be described, it will be assumed that non-destructive inspection of tubular member 10 and coupling 12 will be performed by the well-known eddy current method, although this invention is not so limited. Top arm 16 has four individual eddy current probe assemblies 20 evenly distributed along its length, with the active end of each probe, not illustrated, extending downwardly so that it may ride on the outer surfaces of tubular member 10 and coupling 12. In like manner, bottom arm 18 has four equally spaced probe assemblies 22 with respective probe elements 22a–22d extending transversely of the arm and riding on the inner walls of tubular member 10 and coupling 12. Each of the probe assemblies has two or more electrical wires that extend through the center of its respective inspection arm 16 or 18 to form a bundle or cable 40, 42 that exits from the interior of the arm by means of an appropriate connector 44. Preamplifiers 46 and 48 are mounted on brackets 26 and receive the respective cables 40 and 42 to amplify the inspection signals. The outputs of preamplifiers 46 and 48 pass through the hollow interior of rotor member 28 and motor 30 and couple to slip ring-brush assembly 32. Terminals on the stator of assembly 32 are to be connected to signal processing readout and display apparatus, not illustrated.

In a cycle of operation of the end area inspection apparatus illustrated in FIG. 1, support member 34 initially is withdrawn to the right of the position illustrated in FIG. 1 so that arms 16 and 18 are away from the coupling member 12. Upon initiation of a command signal from the operator, the d.c. motor that controls the rack and pinion drive for support member 34 causes that support to move toward the left so that arms 16 and 18 approach the end of coupling 12 with arm 16 on the outside and arm 18 on the inside. As the arms 16 and 18 advance toward the left, motor 30 rotates rotor member 28 and the entire inspection assembly. Rotating arms 16 and 18 continue advancing so that the eddy current probes 20a–d on arm 16 engage the outer surfaces of coupling 12 and tubular member 10 and the probes 22a–22d on arm 18 engage the inner surfaces. The rate of axial advance and rotation of the inspection assembly are so proportioned that the helical paths transversed by the eddy current probes will provide substantially complete inspection coverage of the end area of tubular member 10 and coupling 12. Arms 16 and 18 continue their helical advance into tubular member 10 until the right end of coupling 12 contacts a limit switch 50 that is attached to transverse bracket member 26 between the right ends of arms 16 and 18. Actuation of limit switch 50 causes the motor that controls the movement of support member 34 to reverse its direction of rotation so that the rack and pinion mechanism reverses direction to cause rotating arms 16 and 18 to begin moving toward the right in FIG. 1 so as to withdraw from tubular member 10 and coupling 12. Inspection signals from the probes may be collected during both the advance and withdrawal of arms 16 and 18, or only during withdrawal.

Figure 2:
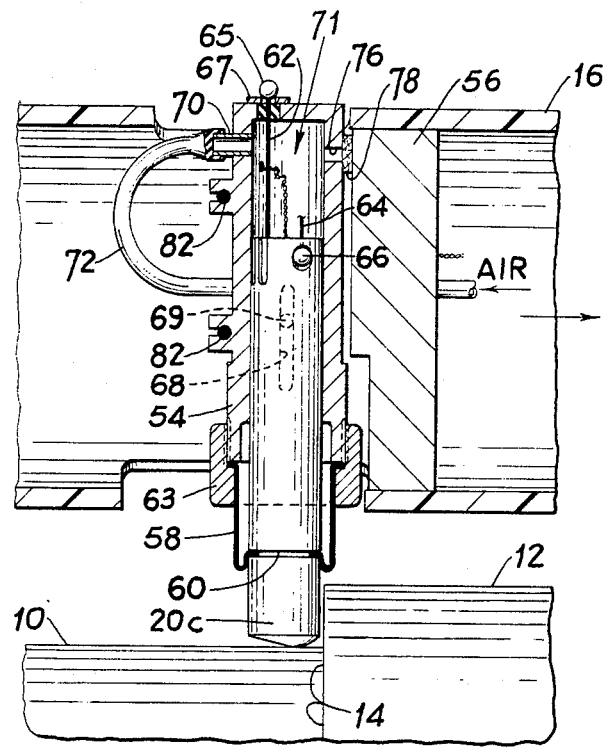
FIG. 2 is a sectional view of a portion of the end area inspection apparatus of FIG. 1 presenting a partially cut away view of an inspection probe of this invention.

In FIG. 1, the region 14 of tubular member 10 at and immediately adjacent the inward end of coupling 12 is the region that heretofore has been extremely difficult or impossible to inspect with automatic inspection apparatus, thereby necessitating manual inspection of that region. Because all the probe assemblies on the two arms 16 and 18 are identical, only one will be explained in detail. As illustrated in FIG. 2, it is seen that the inspection probe 22c for example, must get in as close as possible to the shoulder or left end of coupling 12 in order to inspect the region 14. The probe then somehow must be raised in a radial direction to be in position on the outer surface of coupling 12 to continue its helical path along the coupling. The inspection probe assembly of this invention includes an outer housing 54 that is secured transversely across the interior of arm 16 by means of a mounting bracket 56 that is secured to the arm by means of bolts 57. One end of probe housing 54 is open, the bottom end in FIG. 2, and the probe 20c extends upwardly into the interior of housing 54. A bellows 58 of an elastomeric material such as rubber is engaged at its bottom end in a circumferential slot 60 in probe 20c and its top end is retained between the end of probe housing 54 and an internally threaded retaining ring 63. Bellows 58 and probe 20c are illustrated in FIG. 2 in their most extended position when inspecting the outer wall of tubular member 10. In this extended position, probe member 20c is forced outwardly from housing 54 against the forces applied by elastomeric bands 62 and 64. These bands have enlarged ends 65 and 66 that are secured at one of the ends by means of C-shaped washers 67 to the closed end of probe housing 54 and at their opposite ends to the inner end of probe 20c. A slot or keyway 68 is machined in the side of probe 20c and a screw 69 extends through the wall of housing 54 and engages the keyway so as to limit the transverse motion of probe 20c.

Probe 20c is forced to its outwardly extended position illustrated in FIG. 2 by means of air pressure that is passed through an inlet tube 70 to a chamber 71 in the interior of probe housing 54. Air hose 72 is coupled to inlet tube 70 and extends through the interior of arm 16 to a source of pneumatic pressure, not illustrated. A suitable rotary coupling or union is provided in the pneumatic supply line to permit rotation of air hoses 72 relative to the stationary source. An air escape or exit passage or aperture 76 is located near the closed end of probe housing 54 and normally is blocked by a pad 78 of an elastomeric material, for example, that is secured to mounting bracket 56. When probe 20c is on the outer surface of tubular member 12, probe housing 54 is urged in a clockwise direction around a pivot pin 80, FIG. 3, by means of two elastomeric bands 82 whose enlarged ends 84 are respectively held in retaining members 86 and 88 on mounting bracket 56 and housing 54. Elastomeric bands 82 are under tension to yieldingly hold exit port or aperture 76 against pad 78 so that air admitted through the entrance tube 70 builds up pressure in chamber 71 and forces probe 20c outwardly against the tension of the vertically extending elastomeric bands 62 and 64. Bellows 58 is sufficiently flexible and yielding to permit the free translation of probe 20c.

Figure 4:
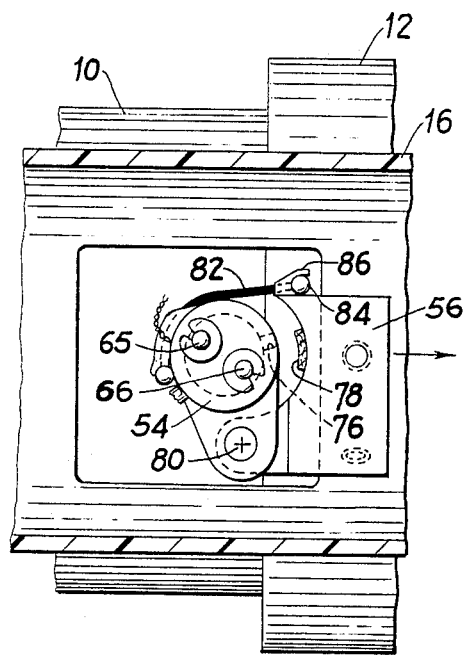

As seen in FIG. 2, as the inspection apparatus moves to the right nd the right side of probe 20c strikes the end shoulder of coupling 12, the probe 20c and its housing 54 cannot continue to move axially with arm 16. Instead, it will pivot in a counterclockwise direction, FIG. 4, about its pivot pin 80 as arm 16 continues its helical motion toward the right in FIG. 2. This counterclockwise pivoting of housing 54 causes escape port or aperture 76 to move away from pad 78 so that the air under pressure in chamber 71 within housing 54 now escapes through port 76. The internal air pressure within housing 54 no longer is sufficient to hold probe 20c in its extended position against the tension of vertical elastomeric bands 62 and 64. Consequently, probe 20c is drawn upwardly further into housing 54 until the bottom end of the probe clears the left end of coupling 12. When this occurs, probe housing 54 is free to rotate in a clockwise direction about pivot pin 80 under the rotational force applied by the two elastomeric bands 82. Housing 54 therefore snaps back to its position illustrated in FIG. 3 wherein exit port 76 again is blocked by pad 78. Air pressure again builds up in fluid chamber 71 and probe 20c is pushed radially outwardly against the tension of elastomeric bands 62 and 64. The end of probe 20c now will contact the outer surface of coupling 12, as illustrated in FIG. 5. It is seen that bellows 58 is partially turned inside of itself to maintain a sealing engagement between probe 20c and retaining ring 65.

Because the inspection of region 14 on tubular member 10 at the inward end of coupling 14, FIG. 1 is of major concern in the inspection of the end area and coupling, it is desirable that the inspection probes each make a full circumferential passage around the tubular member after it encounters the end wall of the coupling and before it hops up onto the outer surface of the coupling. This is accomplished in the illustrated embodiment of the invention in the following manner. To insure complete inspection coverage of the pipe end area and coupling without an unduly large number of inspection probes, the helical paths of the probes on arms 16 or 18 have a pitch of one-tenth inch, for example. This means that the arms 16 and 18 will move axially one-tenth inch when a probe is against the end of coupling 12 and makes one revolution of tubular member 10. This one revolution of a probe that is against the end of the coupling must occur before probe housing 54 pivots away from pad 78, FIG. 2, to unblock air escape port 76. The desired objective is accomplished by making pad 78 of a "spongy" elastomeric material that has sufficient thickness and compliance to yield at least one-tenth inch when probe housing 54 is urged into contact with the pad. Accordingly, when a probe encounters the end of a coupling and the housing 54 begins to pivot away from support bracket 56, pad 78 will maintain a blocking relationship with escape port 76 for at least one-tenth of an inch axial motion while the compressed pad is being restored to its normal, uncompressed state. Further axial motion causes escape port 76 to be clear of pad 78 and free to bleed off the air pressure in chamber 71. Other means may be employed to delay the unblocking of exit port 76 until a probe has made at least one complete revolution around the pipe while that probe is in contact with the end of the coupling.

It is thus seen that the "hopping" action of the probe to hop over the end of coupling 12 is self actuating and permits probe 20c to move into and around the region 14 on pipe 10 adjacent coupling 12. This self actuating hopping feature is a distinct advantage over other mechanisms such as a camming means that lifts the probe off of tubular member 10 in response to some separate feeler member that senses the end of casing 12. The cam must be adjusted so as to raise the probe at the proper time, raise it the proper height above the surface of the tubular member, and then lower it the proper distance to contact the outer surface of coupling member 12. As explained above, the hopping mechanism of this invention is self actuating once the probe contacts the end of the coupling and pivots housing 54 a given distance.

Probes 22a–22d that follow a helical path on the inner surface of tubular member 10 will not hop over the end of coupling 12 but rather they will extend outwardly even further when they pass from the end of tubular member 10 to the inner surface of coupling 12 as arm 18 is withdrawn to the right in FIG. 1. The parameters of elastomeric bands 62 and 64 that yieldingly restrain the probes 22a–22d within the housings 54 and the air pressure within the chambers 71 are proportioned to permit the probes to immediately snap out to the inner wall of casing 12. Folded bellows 58 of the respective probes are long enough to permit such motion.

The above discussion describes air as the fluid for forcing probes 20a–20d and 22a–22d outwardly. Obviously, liquid fluids and other gaseous fluids could be used if desired. Additionally, elastomeric bands 62, 64 and 82 have been illustrated for resiliently restraining the probes within the probe housings, and for resiliently urging the housings against their respective pads 78. Other types of elastic or spring like means may be employed without departing from the teachings of my invention.

The interior of the eddy current probe is illustrated in simplified form in FIG. 5 wherein multiple coils are wound on a coil bobbin and a ferrite rod 80 passes axially through the bobbin. A suitable eddy current inspection device is illustrated and described in more detail in U.S. patent application No. 457,321 entitled Lift-Off Compensation of Eddy Current Probes, in the name of James A. Bains, and which is incorporated herein by reference. It is seen that the interior void space at the bottom region of probe 20C is nonsymetrical, with the thinnest wall being on the right so that the ferrite rod 80 may approach as close as possible to the end of coupling 12 before it hops up onto the coupling. This will permit eddy currents to be produced in the region 14 of tubular member 10, FIG. 2.

Although the eddy current inspection technique described in the above mentioned Bains application presently is preferred in the end area inspection apparatus described above, other types of inspection devices and techniques may be carried by probes 20 and 22 without departing from the teachings of this invention. As is will understood in the art, probes 20 and 22 are made from a hardened, wear resistant material that will provide long life as they ride on the pipe and coupling surfaces.

In its broader aspects, this invention is not limited to the specific embodiment illustrated and described. Various changes and modifications may be made without departing from the inventive principles herein disclosed.

I claim:

1. In the nondestructive inspection of a tubular member having a cylindrical coupling of a different diameter secured to one end of the tubular member, wherein an inspection probe moves along the surface of the tubular member and encounters the end of the coupling as an obstacle to its further movement in a direction parallel to the tubular member axis, an improved mechanism for causing the probe to hop over the obstructing end of the coupling and onto the surface thereof, comprising the combination a probe member adapted to include nondestructive tubular member inspection means, a probe housing adaptive to receive said probe member, the probe member being translatable relative to the housing onto and away from the surface of a tubular member placed adjacent said housing, support means for supporting said housing for movement between first and second positions, means for translating said support means with said housing and probe member parallel to the axis of a tubular member to be inspected, the obstructing end of the coupling forcing the housing to its second position when the moving probe member encounters said obstructing end, and means operable only when the housing moves to its second position for withdrawing the probe from the surface of the tubular member and radially clear of the obstructing end of the coupling and for extending the probe member to the surface of the coupling when the housing returns to its first position once the obstructing end of the housing is cleared.

2. The combination claimed in claim 1 wherein said means for withdrawing the probe member from and extending it to the surface of the tubular member includes,
   a fluid pressure chamber in said housing,
   said probe member being received in the housing by yieldable restraining means and in communication with the chamber so that fluid pressure within the chamber tends to force the probe member outwardly from the housing against the yieldable restraining means that holds it in the housing, and
   means for relieving fluid pressure within said chamber only when the housing is in its second position and for building up pressure in the chamber to force the probe member outwardly from the housing when the housing is in its first position.

3. The combination claimed in claim 2 wherein the means for relieving pressure in said chamber includes,
   a fluid escape port in communication with said chamber,
   escape port blocking means fixed relative to said support means and in blocking relationship to the escape port when the housing is in its first position, whereby fluid pressure builds up in the chamber and forces the probe member outwardly when the housing is in its first position,
   said escape port being free of the blocking action of the blocking means when the housing is in its second position.

4. The combination claimed in claim 3 wherein said blocking means is an elastomeric pad.

5. The combination claimed in claim 4 and including,
   means for yieldingly urging the housing and escape port against the elastomeric pad when the housing is in its first position and for returning the housing to the first position from the second position when the probe member radially clears said obstructing end of the coupling.

6. In the nondestructive inspection of a tubular member having a cylindrical coupling of greater outer diameter secured to one end of the tubular member, wherein an inspection probe moves along the outer surface of the tubular member and over the end and onto the surface of the coupling, an improved mechanism for causing the probe to hop over the end of the coupling and onto the outer surface thereof, comprising the combination
   an elongated probe member adapted to include nondestructive tubular member inspection means,
   a probe housing adaptive to receive therein at least one end of said probe member,
   the probe member being translatable in the housing onto and away from the surface of a tubular member placed adjacent said housing,
   a fluid chamber in said housing between the inner end of the probe member and a portion of the housing,
   support means for pivotally supporting said housing to permit the housing to pivot about an axis between first and second positions,
   first resilient means for holding said probe member in a retracted position in said housing,
   means for admitting a fluid under pressure to said chamber to force the probe means outwardly from the chamber against the force of the first resilient means,
   means for reducing the fluid pressure in said fluid chamber only when the housing moves to the second position to permit the first resilient means to retract the probe means a predetermined distance into the housing,
   means for translating said support means and said housing with the probe member therein parallel to the axis of a tubular member to be inspected,
   means including second resilient means for resiliently holding said housing in said first position when the probe is on the surface of the tubular member and displaced from the coupling, and for permitting the housing to pivot to said second position against the force of the second resilient means when the probe encounters the end of the coupling as the translating support means moves the probe member parallel to the axis of the tubular member and against said one end of the tubular member, thereby to permit fluid under pressure to escape from the chamber,
   said predetermined distance being sufficient to permit the probe to withdraw transversely away from the encountered end of the coupling, thereby permitting said second resilient means to move the housing to its first position to permit fluid pressure to increase in the chamber to urge the probe member outwardly until it contacts the surface of the coupling.

7. In the nondestructive inspection of a tubular member having a cylindrical coupling of a different diameter secured to one end of the tubular member, wherein an inspection probe moves in an axial direction along the surface of the tubular member and encounters the end of the coupling as an obstacle to its further movement in a direction parallel to the tubular member axis, an improved mechanism for causing the probe to hop over the obstructing end of the coupling and onto the surface thereof, comprising the combination
   an elongate probe member adapted to include nondestructive tubular member inspection means,
   a probe housing adaptive to receive therein at least one end of said probe member,
   the probe member being translatable in the housing onto and away from the surface of a tubular member placed adjacent said housing,
   support means for pivotally supporting said housing for movement between first and second positions,
   means for translating said support means and said housing with the probe member therein in a direction parallel to the axis of a tubular member to be inspected, the obstructing end of the coupling forcing the housing to its second position when the moving probe member encounters said obstructing end, and
   means operable only when the housing moves to its second position for withdrawing the probe into its housing and radially clear of the obstructing end of the coupling and for extending the probe member to the surface of the coupling when the housing returns to its first position once the obstructing end of the housing is cleared.

8. In the nondestructive inspection of a tubular member having a cylindrical coupling of a different diameter secured to one end of the tubular member, wherein an inspection probe moves in an axial direction along the surface of the tubular member and encounters the end of the coupling as an obstacle to its further movement in a direction parallel to the tubular member axis, an improved mechanism for causing the probe to hop over the obstructing end of the coupling and onto the surface thereof, comprising the combination

- an elongated probe member adapted to include nondestructive tubular member inspection means,
- a probe housing adaptive to receive therein at least one end of said probe member,
- the probe member being translatable in the housing toward and away from the surface of a tubular member placed adjacent said housing,
- a fluid chamber in said housing between the inner end of the probe member and a portion of the housing,
- means for yieldingly holding said probe member in a retracted position in said housing,
- means for admitting a fluid under pressure to said chamber to force the probe means outwardly from its retracted position in the chamber,
- means for pivotally supporting said housing to permit the housing to pivot about an axis,
- means for translating said support means in a direction parallel to the axis of a tubular member to be inspected to thereby translate the probe means along or adjacent the surface of the tubular member,
- an escape port for permitting fluid under pressure to escape from said chamber whereby the fluid pressure within the chamber is reduced and the means for yieldingly holding the probe member retracts the probe member into said housing,
- means for blocking the port when the housing is in a first position and for unblocking the port when the housing is in a second pivoted position,
- means for yieldingly holding the housing in said first position and for permitting the housing to move to said second position when the probe encounters the end of the coupling as an obstacle to its further movement in a direction parallel to the axis of the tubular member.

9. In the nondestructive inspection of a tubular member having a cylindrical coupling of greater outer diameter secured to one end of the tubular member, wherein an inspection probe moves in a helical pattern along the outer surface of the tubular member and over the end and onto the surface of the coupling, an improved mechanism for causing the probe to hop over the end of the coupling and onto the outer surface thereof, comprising the combination

- an elongated probe member adapted to include nondestructive tubular membr inspection means,
- a probe housing adaptive to receive therein at least one end of said probe member,
- the probe member being translatable in the housing onto and away from the surface of a tubular member placed adjacent said housing,
- a changeable-volume fluid chamber in said housing between the inner end of the probe member and a portion of the housing,
- first resilient means for holding said probe member in a retracted position in said housing,
- means for admitting a fluid under pressure to said chamber to force the probe means outwardly from the chamber against the force of the first resilient means,
- support means for pivotally supporting said housing to permit the housing to pivot about an axis,
- means for translating said support means and said housing with the probe member therein in a direction parallel to the axis of a tubular member to be inspected,
- an escape port in said housing in communication with said chamber for permitting fluid under pressure to escape from the chamber,
- a port blocking means for blocking said escape port when the housing is in a first position and for unblocking the escape port to permit escape of fluid under pressure when the housing is in a pivoted second position,
- means including second resilient means for resiliently holding said housing in said first position when the probe is on the surface of the tubular member and away from the coupling, and for permitting the housing to pivot to said second position against the force of thes second resilient means when the probe encounters the end of the coupling as the translating support means moves the probe member parallel to the axis of the tubular member and toward said one end of the tubular member, thereby to permit fluid under pressure to escape from the chamber,
- said first resilient means causing the probe means to be drawn into the housing a predetermined distance when said blocking means is away from the escape port,
- said predetermined distance being sufficient to permit the probe to withdraw transversely away from the encountered end of the coupling, thereby permitting said second resilient means to move the housing to its first position to again block the escape port in the housing and to permit fluid pressure to increase in the chamber to urge the probe member outwardly until it contacts the surface of the coupling.

10. The combination claimed in claim 9 wherein said support means with the housing and probe member supported thereon is translated in a helical path relative to the surface of the tubular member and coupling.

11. The combination claimed in claim 10 including a plurality of probe members and respective housings disposed in an array to provide a plurality of helical inspection paths said tubular member and coupling.

* * * * *